(12) United States Patent
Kim et al.

(10) Patent No.: US 7,650,182 B2
(45) Date of Patent: Jan. 19, 2010

(54) DUAL SENSING FOR BRADY-TACHY PACEMAKER/ICD

(75) Inventors: Jaeho Kim, Redmond, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 651 days.

(21) Appl. No.: 11/177,230

(22) Filed: Jul. 8, 2005

(65) Prior Publication Data

US 2007/0038253 A1 Feb. 15, 2007

(51) Int. Cl.
*A61B 5/0464* (2006.01)

(52) U.S. Cl. .................. 600/518; 600/509; 600/515

(58) Field of Classification Search ............. 600/509, 600/515, 518, 522, 514
See application file for complete search history.

(56) References Cited

U.S. PATENT DOCUMENTS

| 4,291,699 A * | 9/1981 | Geddes et al. ............. 607/6 |
| 4,940,054 A | 7/1990 | Grevis et al. |
| 4,960,123 A * | 10/1990 | Maker ....................... 607/4 |
| 5,086,772 A | 2/1992 | Larnard et al. |
| 5,113,869 A * | 5/1992 | Nappholz et al. .......... 600/508 |
| 5,190,034 A | 3/1993 | Sholder |
| 5,267,559 A | 12/1993 | Jin et al. |
| 5,330,504 A | 7/1994 | Somerville et al. |
| 5,486,199 A * | 1/1996 | Kim et al. ................. 607/5 |
| 5,730,141 A * | 3/1998 | Fain et al. ................. 600/518 |
| 5,738,105 A | 4/1998 | Kroll |
| 6,223,078 B1 * | 4/2001 | Marcovecchio ............. 607/5 |
| 6,230,059 B1 * | 5/2001 | Duffin ....................... 607/60 |
| 6,522,925 B1 | 2/2003 | Gilkerson et al. |
| 6,760,615 B2 | 7/2004 | Ferek-Petric |
| 6,760,622 B2 | 7/2004 | Helland et al. |
| 6,795,732 B2 * | 9/2004 | Stadler et al. ............. 607/17 |
| 7,212,849 B2 * | 5/2007 | Zhang et a ................ 600/515 |
| 2006/0036288 A1 | 2/2006 | Bocek et al. |

\* cited by examiner

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A system detects events related to cardiac activity. The system comprises a primary cardiac signal sensing circuit, at least one secondary cardiac signal sensing circuit having a higher sensitivity than the primary sensing circuit, and a controller circuit coupled to the primary and secondary cardiac signal sensing circuits. The controller circuit determines a rate of depolarization using the primary sensing circuit and detects tachyarrhythmia using the rate. The controller circuit also detects tachyarrhythmia using the secondary sensing circuit and also deems the tachyarrhythmia valid if the controller circuit detects the tachyarrhythmia using both the primary and secondary sensing circuit.

23 Claims, 13 Drawing Sheets

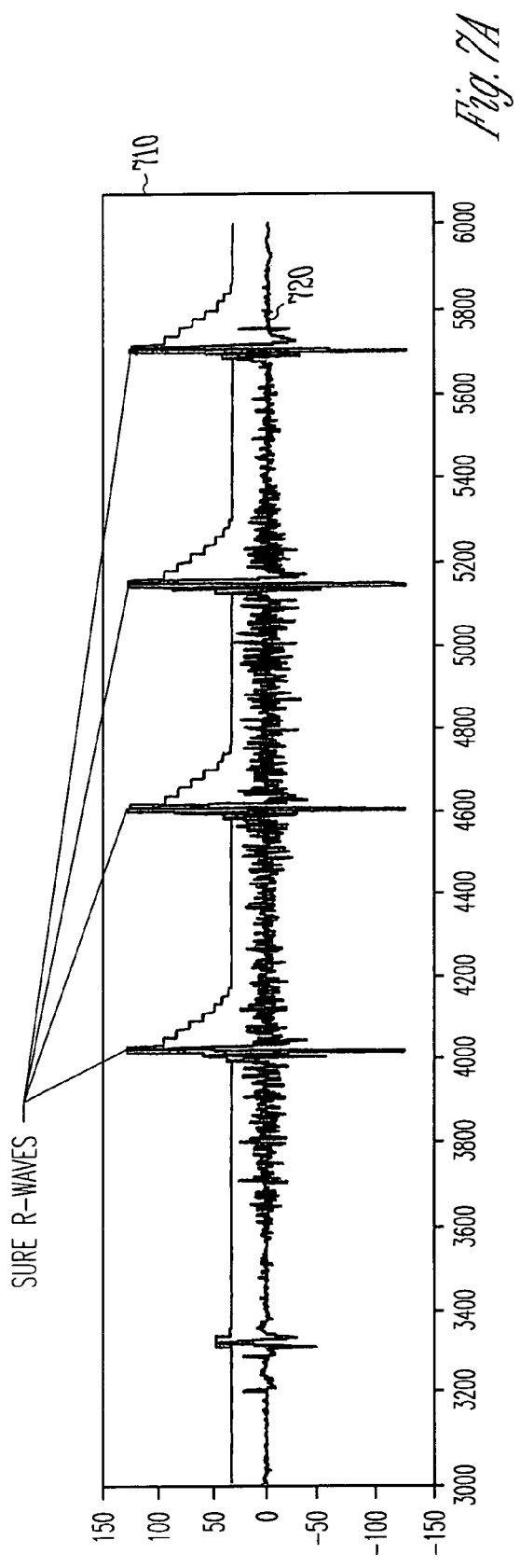
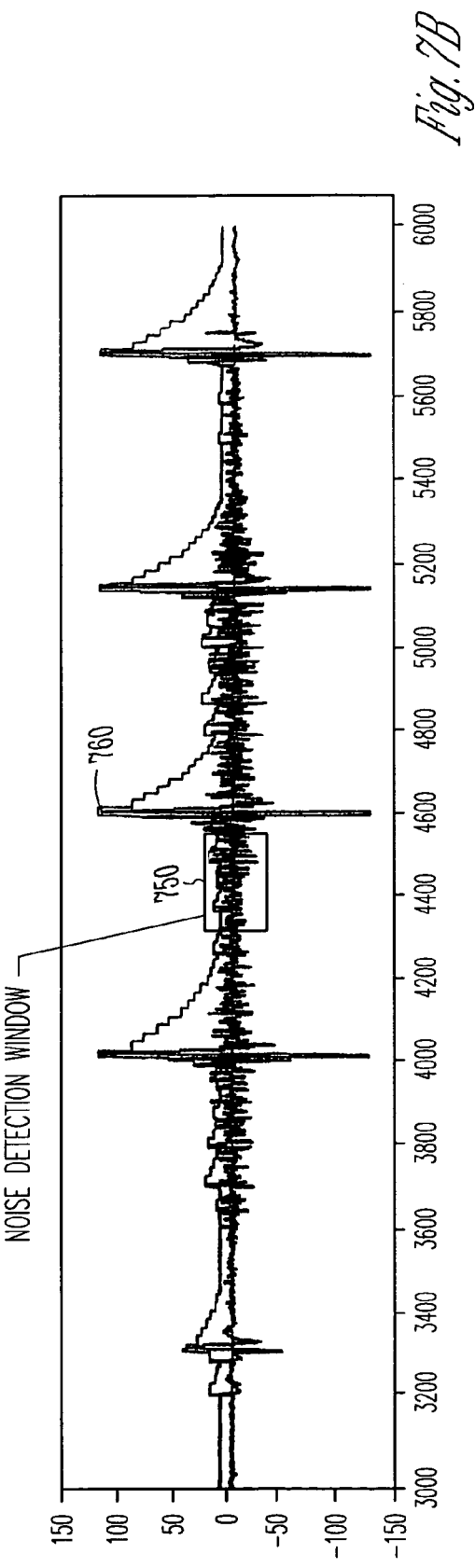
Fig. 7A
Fig. 7B

DUAL SENSING FOR BRADY-TACHY PACEMAKER/ICD

CROSS-REFERENCE TO RELATED APPLICATIONS

This application is related to commonly assigned U.S. Pat. No. 5,486,199, "SYSTEM AND FOR REDUCING FALSE POSITIVES IN ATRIAL FIBRILLATION DETECTION," filed on Jul. 20, 1994, which is hereby incorporated by reference.

TECHNICAL FIELD

The field generally relates to implantable medical devices and, in particular, but not by way of limitation, to systems and methods for detecting events related to cardiac activity.

BACKGROUND

Implantable medical devices (IMDs) are devices designed to be implanted into a patient. Some examples of these devices include cardiac function management (CFM) devices. CFMs include implantable pacemakers, implantable cardioverter defibrillators (ICDs), and devices that include a combination of pacing and defibrillation including cardiac resynchronization therapy. The devices are typically used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Other examples of implantable medical devices include implantable insulin pumps or devices implanted to administer drugs to a patient.

Additionally, some IMDs detect events by monitoring electrical heart activity signals. In CFM devices, these events include heart chamber expansions or contractions. By monitoring cardiac signals indicative of expansions or contractions, IMDs are able to detect abnormally slow heart rate, or bradycardia. The IMDs are also able to detect abnormally rapid heart rate, or tachyarrhythmia. Patients that use IMDs may be adversely affected by over-sensing of the sense amplifiers. Over-sensing occurs when sense-amplifiers incorrectly interpret sensed signals or noise as cardiac signal artifacts, such as P or R-waves indicative of atrial or ventricular heart contractions respectively. Over-sensing can result in a bradycardia device incorrectly inhibiting pacing therapy or a tachyarrhythmia device incorrectly delivering high energy shock therapy. Patients that use IMDs to treat tachyarrhythmia may also be adversely affected by under-sensing. Under-sensing occurs when electrical signals associated with tachyarrhythmia are not sensed by the device and therefore, high-energy shock therapy is not delivered. The present inventors have recognized a need for improved sensing of events related to cardiac activity.

SUMMARY

This document discusses, among other things, systems and methods for detecting events related to cardiac activity. A system embodiment includes a primary cardiac signal sensing circuit for sensing at least a first intrinsic cardiac signal and at least one secondary cardiac signal sensing circuit for sensing at least a second intrinsic cardiac signal. The primary sensing circuit includes first and second implantable electrodes and the second sensing circuit includes at least a third implantable electrode different from the first or second electrode. The system also comprises a controller circuit, coupled to the primary and secondary cardiac signal sensing circuits. The controller circuit determines a rate of depolarization of the heart using the primary sensing circuit and uses the rate to detect tachyarrhythmia. The controller circuit also detects tachyarrhythmia using the secondary sensing circuit and deems the tachyarrhythmia valid if the controller circuit detects the tachyarrhythmia using both the primary and secondary sensing circuit.

A method embodiment includes sensing a first intrinsic cardiac signal associated with a depolarization rate of a heart using a primary sensing circuit that includes first and second implantable electrodes, sensing a secondary intrinsic cardiac signal of the heart using at least one secondary sensing circuit that includes a third implantable electrode, detecting tachyarrhythmia using the primary sensing circuit, determining whether tachyarrhythmia is indicated by the secondary sensing circuit, deeming the tachyarrhythmia as valid if both the primary and secondary sensing circuits indicate tachyarrhythmia, and deeming the tachyarrhythmia as invalid if only the primary sensing circuit indicates tachyarrhythmia.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

FIGS. 7A and 7B show examples of electrograms of cardiac signals.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for improved detection of cardiac events. The efficacy of a medical device in treating abnormally rapid heart rates is often expressed in terms of sensitivity and specificity. Sensitivity refers to the ability of the detection scheme of a device to effectively detect an abnormal heart rhythm that the device is to treat (e.g., ventricular tachycardia or ventricular fibrillation, or to distinguish these abnormal rhythms from noise). Specificity refers to the ability of the detection scheme of a device to avoid treating those rhythms that the device is not intended to treat (e.g., sinus tachycardia). In practice, designing a detection scheme for a medical device involves settling for a trade-off between sensitivity and specificity. Because failing to correctly treat an abnormal heart rhythm that the device is to treat may result in sudden cardiac death (SCD), detection schemes are designed to error on the side of increasing sensitivity with the result that more rhythms are treated than necessary to avoid SCD. Thus, designers of detection schemes ensure that the benefit of such schemes (i.e., properly treating life threatening arrhythmias) outweighs the cost of the schemes (i.e., inappropriately delivering therapy, especially painful shock therapy).

As discussed previously, medical devices used in the treatment or the diagnosis of cardiac arrhythmias are typically susceptible to over-sensing or under-sensing that may cause a medical device to incorrectly respond to a patient's needs. Because time is an important factor in providing anti-tachyarrhythmia therapy, it is important to quickly and correctly identify the tachyarrhythmia episodes. As medical devices continue to advance, more information is provided due to improved cardiac signal sensing ability of such devices. Improved use of the information can result in detecting tachyarrhythmia with higher sensitivity, higher specificity, or both higher sensitivity and higher specificity.

Figure 1:
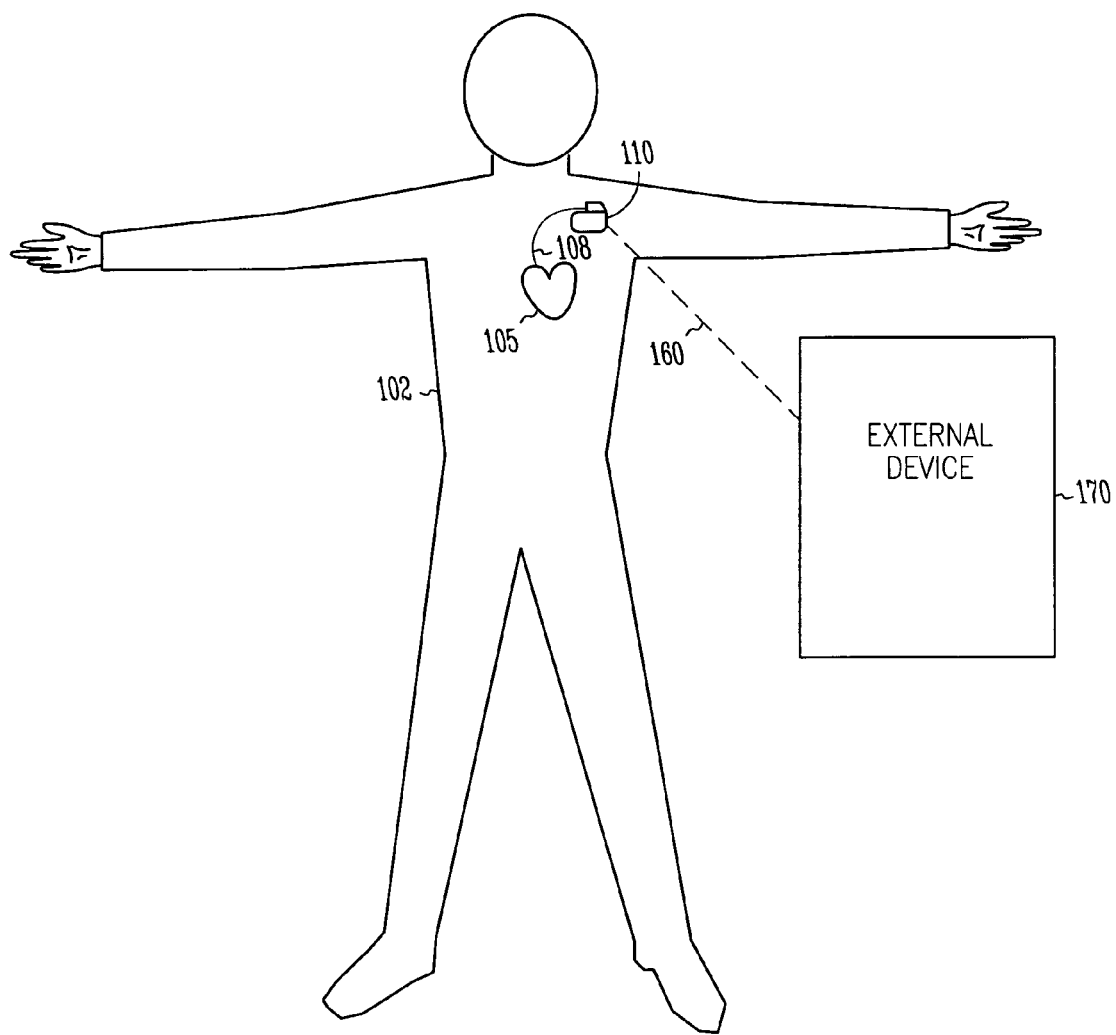
FIG. 1 illustrates an embodiment of portions of a system that uses an implantable medical device.

FIG. 1 illustrates an embodiment of portions of a system 100 that uses an implantable medical device (IMD) 110. As one example, the system 100 shown is used to treat a cardiac arrhythmia. The IMD 110 includes an electronics unit coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing electrical activity of the heart 105.

Figure 2A:
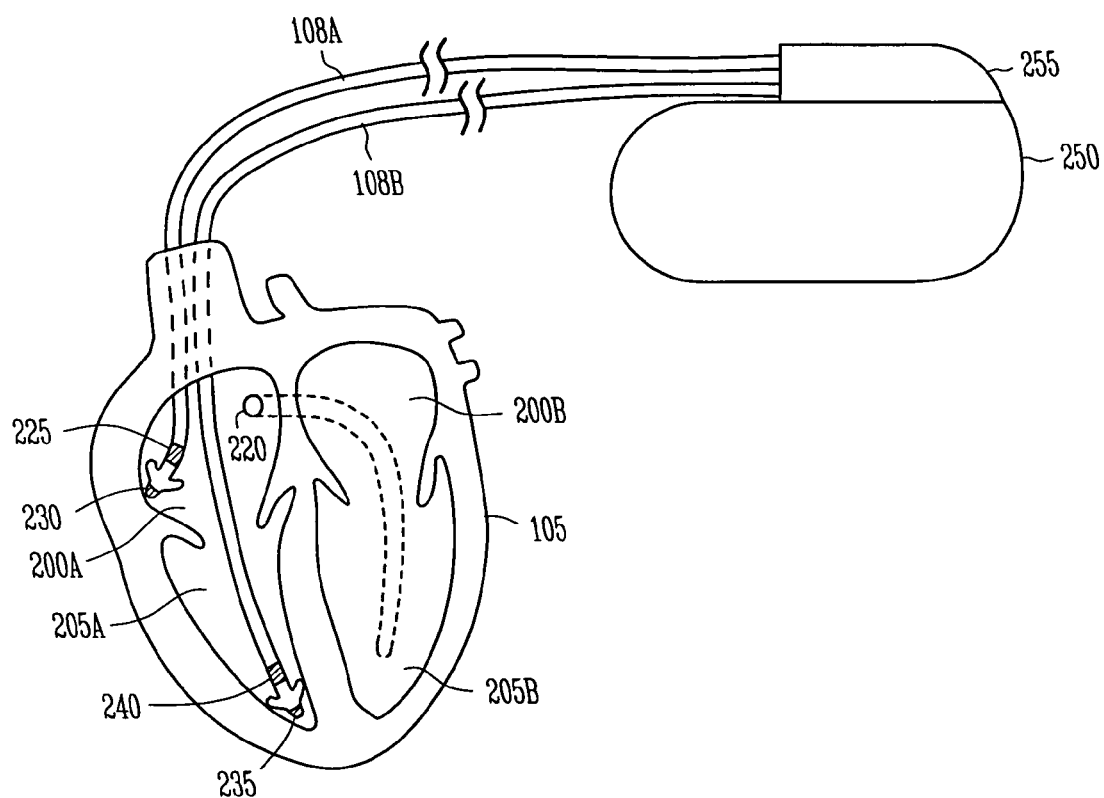
FIGS. 2A and 2B illustrate an implantable medical device coupled by one or more leads to a heart.
Figure 2B:
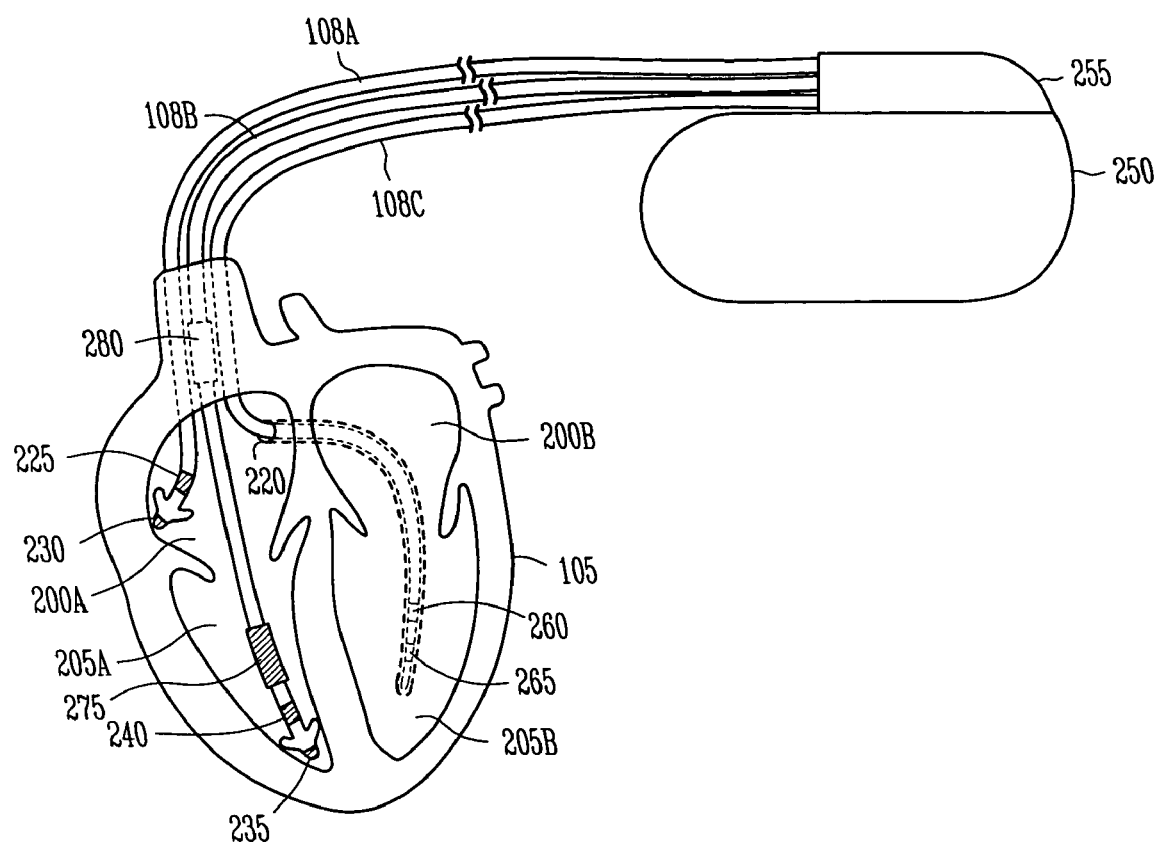

FIGS. 2A-B illustrate IMDs 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. In the embodiment of FIG. 2A, atrial lead 108A includes electrodes (electrical contacts, such as ring electrode 225 and tip electrode 230) disposed in an atrium 200A of heart 105 for sensing signals, or delivering pacing therapy, or both, to the atrium 200A.

Ventricular lead 108B includes one or more electrodes, such as tip electrode 235 and ring electrode 240, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105.

The embodiment of FIG. 2B includes a third cardiac lead 108C attached to the IMD 110 through the header 255. The third lead 108C includes ring electrodes 260 and 265 placed in a coronary vein lying epicardially on the left ventricle (LV) 205B via the coronary vein 220.

In the embodiment of FIG. 2B, lead 108B further includes a first defibrillation coil electrode 275 located proximal to tip and ring electrodes 235, 240 for placement in a right ventricle (RV), and a second defibrillation coil electrode 280 located proximal to the first defibrillation coil 275, tip electrode 235, and ring electrode 240 for placement in the superior vena cava (SVC). In some examples, high energy shock therapy is delivered from the first or RV coil 275 to the second or SVC coil 280. In some examples, the SVC coil 280 is electrically tied to an electrode formed on the IMD can 250. This improves defibrillation by delivering current from the RV coil 275 more uniformly over the ventricular myocardium. In some examples, the therapy is delivered from the RV coil 275 only to the electrode formed on the IMD can 250.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 235 to a right ventricular ring electrode 240 would be a first vector, and sensing from an RV coil 275 to an electrode on the can 250, or a header 255, would be second vector.

Figure 3:
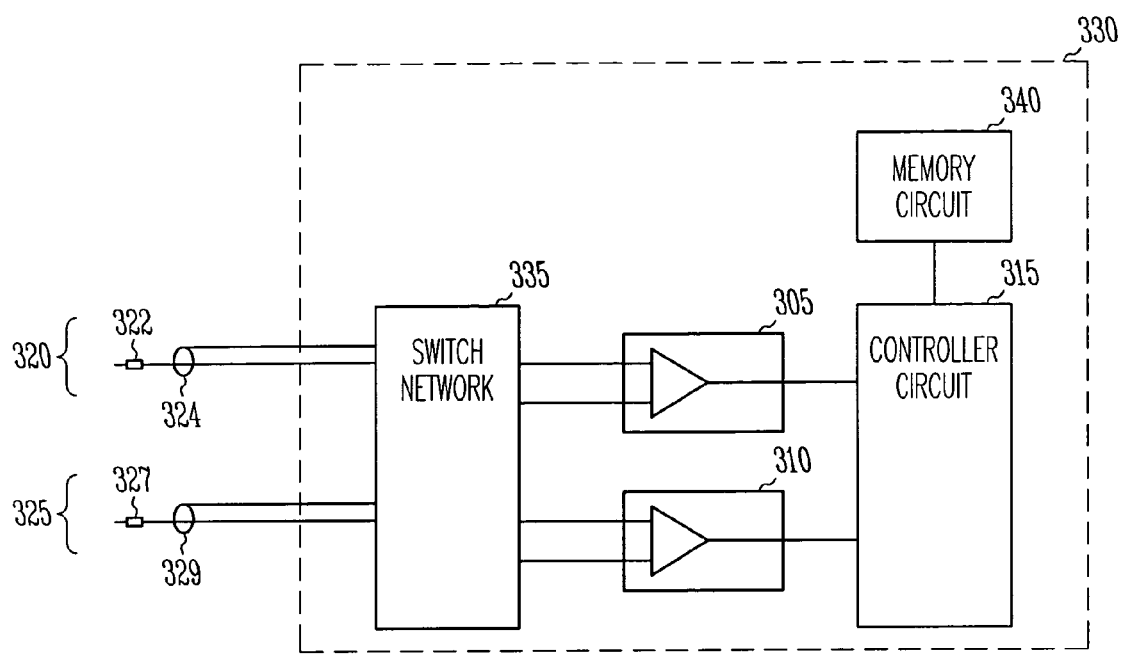
FIG. 3 shows a block diagram of an embodiment of a system to detect cardiac events.

FIG. 3 shows a block diagram of an embodiment of a system 300 to detect cardiac events. The system 300 comprises a primary cardiac signal sensing circuit 305 operable to sense at least a first intrinsic cardiac signal, at least one secondary cardiac signal sensing circuit 310 operable to sense at least a second intrinsic cardiac signal, and a controller circuit 315 coupled to the primary and secondary cardiac signal sensing circuits 305, 310. In some examples, electrodes are incorporated into one or more leads, such as bipolar leads 320, 325. The bipolar leads 320, 325 include tip electrodes 322, 327 and ring electrodes 324, 329. In some examples, the system 300 includes an implantable medical device and the electrodes include a can electrode 330. In some examples, the system 300 includes a switch network 335 that couples the sensing circuits 305, 310 to any combination of one or more electrodes. The switching network 335 allows the sensing circuits 305, 310 to sense cardiac signals from a plurality of sense vectors.

The primary and secondary sensing circuits 305, 310 include implantable electrodes to provide electrical contact with a heart. The primary sensing circuit 305 includes at least first and second electrodes such as, for example, lead tip electrode 322 and lead ring electrode 324. The secondary sensing circuit 310 includes at least one electrode different from the electrodes included in the primary sensing circuit 305, such as an electrode formed on the can. This provides for the secondary sensing circuit 310 sensing along a different vector than the primary sensing circuit 305.

The first intrinsic cardiac signal sensed by the primary sensing circuit 305 is associated with depolarization of a first ventricle of a heart. Examples of the primary cardiac signal sensing circuit 305 include one or more sensing circuits that sense right or left ventricular depolarizations, such as are typically used in devices to treat bradycardia through pacing therapy and in devices to treat congestive heart failure through resynchronization therapy. In general, these electrodes and sensing circuits are intended to monitor the heart rate of a patient, and for this reason the electrodes, the placement of the electrodes, and the sensing circuits comprise a sense vector sometimes referred to as a "rate channel." The primary sensing circuit 305 can be used to detect tachyarrhythmia from the sensed depolarizations. For example, ventricular tachycardia can be detected by comparing sensed P-waves (atrial depolarizations) and R-waves (ventricular depolarizations). A sudden high ventricular rate with dissociation between P-waves and R-waves may indicate tachycardia. A description of systems and methods that detect tachycardia using rate channels is found in Gilkerson, et al., U.S. Pat. No. 6,522,925, "System and Method for Detection Enhancement Programming," filed May 13, 2000, which is incorporated herein by reference.

The secondary sensing circuit 310 includes a different vector than the primary sensing circuit 305. In some examples, the secondary sensing circuit 310 includes at least one electrode that can deliver high energy shock therapy. In some examples, the secondary sensing circuit 310 includes a coil electrode for placement in a right ventricle, e.g. the RV coil 275 in FIG. 2B. In some examples, the secondary sensing circuit 310 includes a coil electrode for placement in a superior vena cava, e.g. the SVC coil 280 of FIG. 2B. Circuits that include such electrodes are sometime s referred to as "shock channels." In some examples, secondary sensing circuit 310 includes an electrode for placement in a left ventricle.

In some examples, the secondary sensing circuit 310 of FIG. 3 has higher sensitivity than the primary sensing circuit 305 in order to detect ventricular tachycardia. Having the higher sensitivity on the secondary circuit 310 avoids compromising the sensitivity of the primary circuit 305. In some examples, higher sensitivity refers to the secondary sensing circuit 310 having a lower signal sensing threshold than the primary circuit 305, or the secondary sensing circuit 310 providing greater amplification to detected cardiac signals, or the secondary sensing circuit 310 having both a lower signal sensing threshold and providing greater amplification than the primary sensing circuit 305.

However, if the primary and secondary sensing circuits 305, 310 include different vectors (for example RV tip to RV coil for the primary sensing circuit 310 and RV coil to SVC coil tied to can for the secondary circuit 310), and are filtered differently (for example, filtering the primary circuit from 20-100 Hz and filtering the secondary circuit from 3-80 Hz), then the amplitudes of sensed signals (such as R-waves) are likely to be different between the two sensing circuits 305, 310. In such a case, setting one sensing threshold lower relative to the other does not necessarily result in higher sensitivity. An alternative is to set the sensing thresholds relative to a signal sensed on the circuits.

As an illustrative example, the sensing threshold for the primary sensing circuit 305 can be set relative to R-wave amplitudes sensed on that circuit 305 (such as 15% of the average R-wave amplitude), and the sensing threshold for the secondary sensing circuit 310 can be set relative to R-wave amplitudes sensed on that circuit 310 (such as 10% of the average R-wave amplitude). Thus, in some examples, higher sensitivity refers to setting a lower sensing threshold relative to the amplitude of signals sensed on the circuits 305,310 rather than relative to each other.

The controller circuit 315 is operable to detect tachyarrhythmia using the primary sensing circuit 305 and to detect tachyarrhythmia using the secondary sensing circuit 310. The term "operable" refers to the controller circuit 315 executing an algorithm or algorithms implemented by hardware, software, firmware or any combination of hardware, software or firmware. The controller circuit 315 deems the tachyarrhythmia valid if the controller circuit 315 detects the tachyarrhythmia using both the primary and secondary sensing circuits 305, 310 or deems the tachyarrhythmia invalid (i.e., the episode does not indicate tachyarrhythmia, or is questionable and requires further confirmation) if the controller circuit 315 only detects the tachyarrhythmia using the primary sensing circuit 305. Specificity to detect tachyarrhythmia is improved when multiple sensing vectors are used. If two vectors do not agree on an indication of tachyarrhythmia, additional analysis can be performed to arrive at a final decision. According to some examples of the system 300, a therapy circuit is coupled to the controller circuit 315. The controller circuit 315 initiates delivery of a therapy to the heart using the therapy circuit when the tachyarrhythmia is deemed valid. In some examples, the therapy circuit provides high-energy shock therapy. In some examples, the system provides anti-tachy pacing (ATP). In some examples, the therapy circuit initiates delivery of a drug to treat tachyarrhythmia.

According to some examples, the secondary sensing circuit 310 is included in sense vectors other than a shock channel. In some examples, the secondary sensing circuit 310 senses impedance signals across a vector that includes the myocardium of a patient (i.e. an "impedance channel"). The controller circuit 315 measures mechanical action of a heart using the impedance signals. Tachyarrhythmia can be deduced from the detected mechanical action. In other examples, the secondary sensing circuit 310 includes a wireless ECG system. Descriptions of wireless ECG systems can be found in commonly assigned, co-pending U.S. patent application Ser. No. 10/975,166, Zhang et al., "METHODS AND APPARATUSES FOR ARRHYTHMIA DETECTION AND CLASSIFICATION USING WIRELESS ECG," which is incorporated herein by reference.

The number of vectors used to make a decision about tachycardia is not limited to only two vectors. In some examples, the secondary sensing circuit includes a plurality of secondary sensing circuits to detect tachyarrhythmia. The controller circuit 315 deems the tachyarrhythmia valid using the primary sensing circuit 305 and at least one of the secondary sensing circuits 310.

When noise is present on one sensing vector, another sensing vector may be free from noise. The controller circuit 315 makes a decision concerning the validity of the tachyarrhythmia based on the noise free measurement. For example, if tachyarrhythmia is detected by the primary sensing circuit 305 but not by the secondary sensing 310, the controller circuit 315 deems the incident to be noise rather than an episode of tachyarrhythmia. In some system examples, the controller circuit 315 arrives at a final decision by additional analysis. In some examples of additional analysis, arriving at a final decision includes analysis to improve the signal-to-noise ratio of measured cardiac signals. In some examples of improving the signal-to-noise ratio, the controller circuit 315 includes a circuit to implement a multiplying function and multiplies the second sensed cardiac signal and the first sensed cardiac signal together point-by-point. In some examples, the signal-to-noise ratio is improved by shifting the second cardiac signal in time to line up with the first cardiac signal before multiplying the second cardiac signal and the first cardiac signal.

Figure 4:
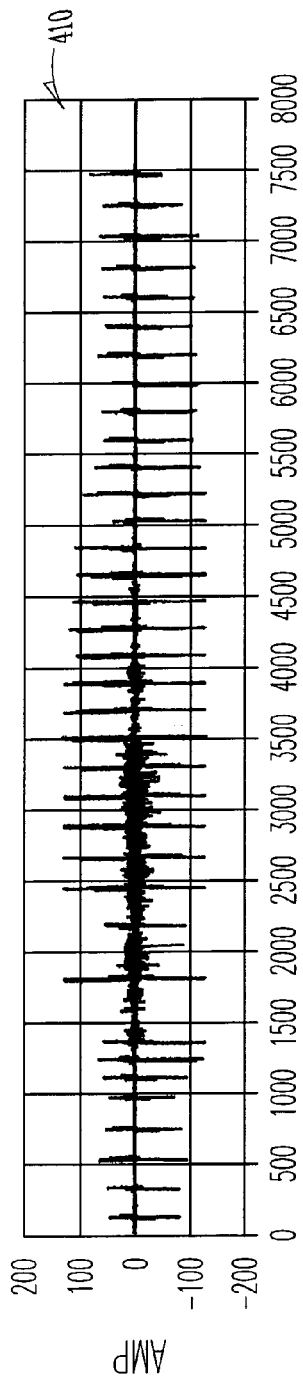
FIG. 4 shows examples of electrograms of cardiac signals.
Figure 4:
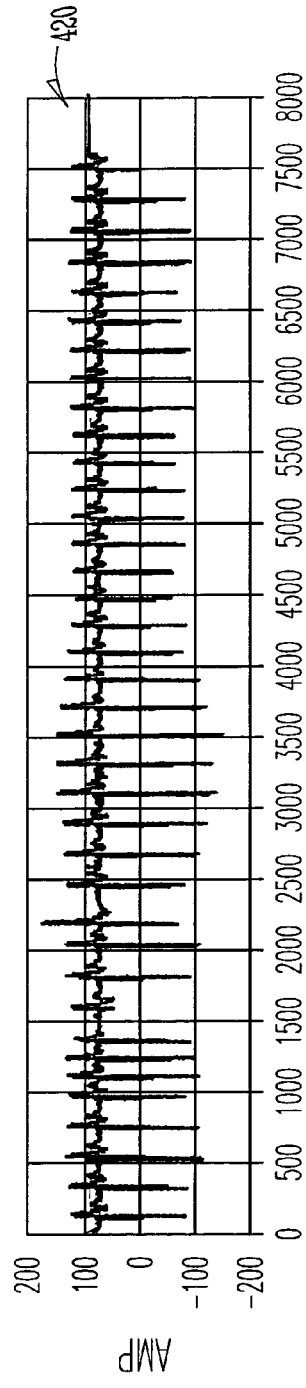
Figure 4:
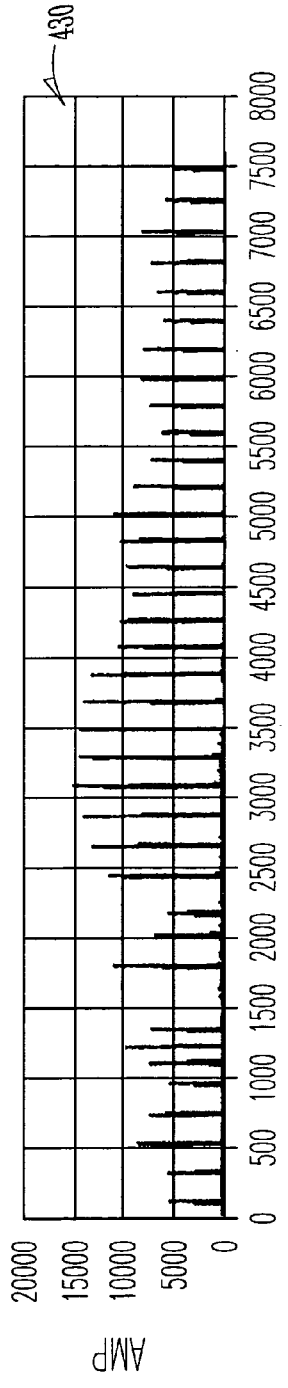

FIG. 4 shows graphs 400 of electrogram readings (EGMs) of intrinsic cardiac signals. Electrograms are sensed intrinsic cardiac electrical signals that are sampled by a device coupled to implantable electrodes. The sampled signals are quantized for display, such as a strip chart display for example. Graph 410 shows an EGM of a first cardiac signal sensed using a primary sensing circuit (representing a signal sensed from a rate channel sense vector). Graph 420 shows an EGM of an intrinsic cardiac signal sensed using a secondary sensing circuit (representing a signal sensed from a shock channel sense vector). Graph 430 shows an EGM that is the result of shifting and multiplying the EGM signal in 420 by the EGM in 410. In some examples, the time shifting between two channels maximizes the absolute peak value of the multiplied signal during a normal rhythm. The graph 430 shows that, in the example, the signal-to-noise ratio is improved from about 5-to-1 in graphs 410, 420 to about 50-to-1. This analysis can be done using signals sensed from any two sense vectors. The analysis can also be done using signals processed with different signal processing procedures. For example, two signals could be analyzed where the first signal is a bandpass filtered version of the second signal.

Returning to the system of FIG. 3, the controller circuit 315 performs analysis, such as multiplication, on the cardiac signals as they are obtained in real time or by analyzing stored representations of the signals. Some system examples further include a memory circuit 340 to store representations of at least the first and second intrinsic cardiac signals. The controller circuit 315 analyzes the stored representations to arrive at a final decision concerning the detection of tachyarrhythmia. In some examples, the memory circuit includes a circular buffer. In a circular buffer, the oldest stored value in memory is the first element replaced. Thus, the oldest sample of a sensed intrinsic signal stored by the controller circuit 315 is the first element replaced by the controller circuit 315. In this way, the memory circuit 340 stores a running segment or "window" of the cardiac signals as they are measured in real time. The width of the segment may be of a predetermined time duration, such as, for example, eight seconds. In some system examples, the controller circuit 315 continuously updates and analyzes the stored representations in real-time. In some examples, the controller circuit 315 analyzes the stored representations periodically. In some examples, the memory contents are transferred to an external device and the analysis is performed not in real time but sometime after the occurrence of the tachyarrhythmia episode.

In some examples, the system 300 is an implantable pacemaker with cardioverter/defibrillator circuitry added. These devices are sometimes called PG-ICDs and are of smaller size than typical ICDs and are tailored for bradycardia patients, rather than for tachyarrhythmia patients indicated for an ICD. Because of a smaller size of battery and charging circuitry used in the devices, a longer delay for delivery of high energy shock therapy may result. This additional charging time can be used by the controller circuit 315 to analyze the sensed intrinsic cardiac signals. Descriptions of systems and methods related to PG-ICDs are found in commonly assigned, co-pending U.S. patent application Ser. No. 10/921,777, Bocek et al., "PACER WITH COMBINED DEFIBRILLATOR TAILORED FOR BRADYCARDIA PATIENTS," which is incorporated herein by reference.

Figure 5:
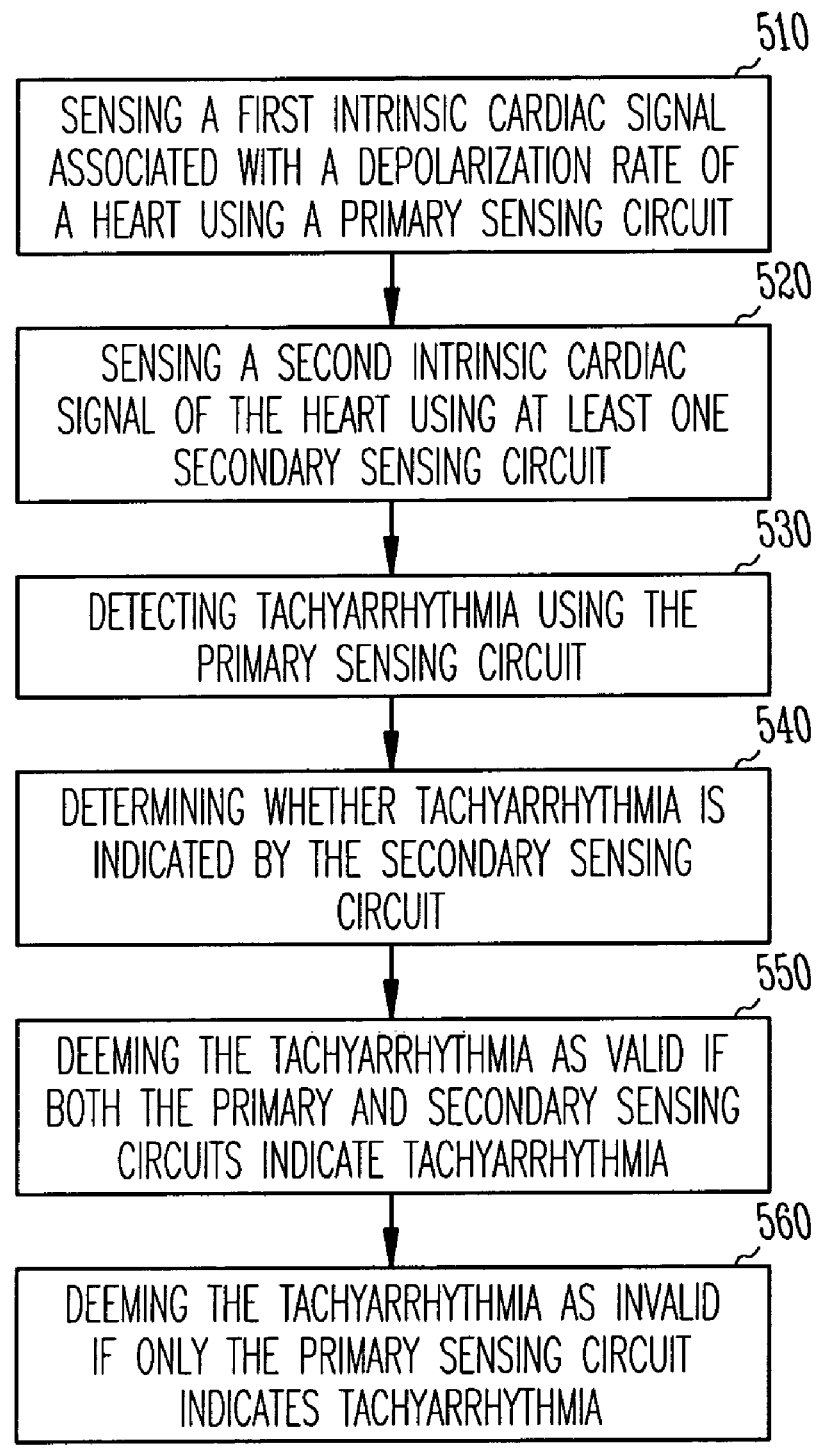
FIG. 5 shows a block diagram of an embodiment of a method for detecting cardiac events.

FIG. 5 shows a block diagram of an embodiment of a method 500 for detecting cardiac events. The method 500 is executed by a medical device. In some embodiments, the medical device is an IMD. In some embodiments, the medical device is an external device operable to communicate with an implantable device. Logical decisions are typically made by a controller such as a microprocessor or the like. At 510, a first intrinsic cardiac signal associated with a depolarization rate of a heart is sensed using a primary sensing circuit. At 520, a second intrinsic cardiac signal of the heart is sensed using at least one secondary sensing circuit. The secondary sensing circuit includes at least one electrode different from the primary sensing circuit electrodes. In some examples, the secondary sensing circuit includes electrodes to sense and treat tachyarrhythmia. These electrode combinations are sometimes referred to as shock vectors or shock channels and, as discussed previously, include electrodes having a larger surface area to handle the higher energies associated with defibrillation therapy. In some examples, the secondary sensing circuit has a different sensitivity than the primary sensing circuit. Typically, the secondary sensing circuit has higher sensitivity than the primary sensing circuit.

At 530, tachyarrhythmia is detected using the primary sensing circuit. At 540, it is determined whether tachyarrhythmia is indicated by the secondary sensing circuit. At 550, if both the primary and secondary sensing circuits indicate tachyarrhythmia, the tachyarrhythmia is deemed valid. At 560, if only the primary sensing circuit indicates tachyarrhythmia, the tachyarrhythmia is deemed invalid. The primary and secondary sensing circuits use any combination of the electrodes discussed previously, and differ from each other by at least one electrode. In some embodiments, the first and second intrinsic cardiac signals are sensed using an IMD. In some embodiments, the intrinsic cardiac signals are sensed using an IMD that provides both cardioversion defibrillation therapy and pacing therapy.

In some embodiments, the method 500 further includes storing representations of the sensed signals. The stored representations of the cardiac signals are sampled over a predetermined time period. Segments of stored representations of the first and second cardiac signals are analyzed to detect or confirm tachyarrhythmia. For example, if the primary sensing circuit detects an episode of tachycardia, the episode is confirmed by comparing stored EGMs obtained using the secondary sensing circuit to the primary sensing circuit. When the primary sensing circuit indicates an episode of tachycardia, a predetermined time period is used to accumulate data for the analysis. In some examples, the time period is four seconds. In some examples the time period is eight seconds. After the time period, the stored signals are compared to see if they both indicate tachyarrhythmia.

Figure 6:
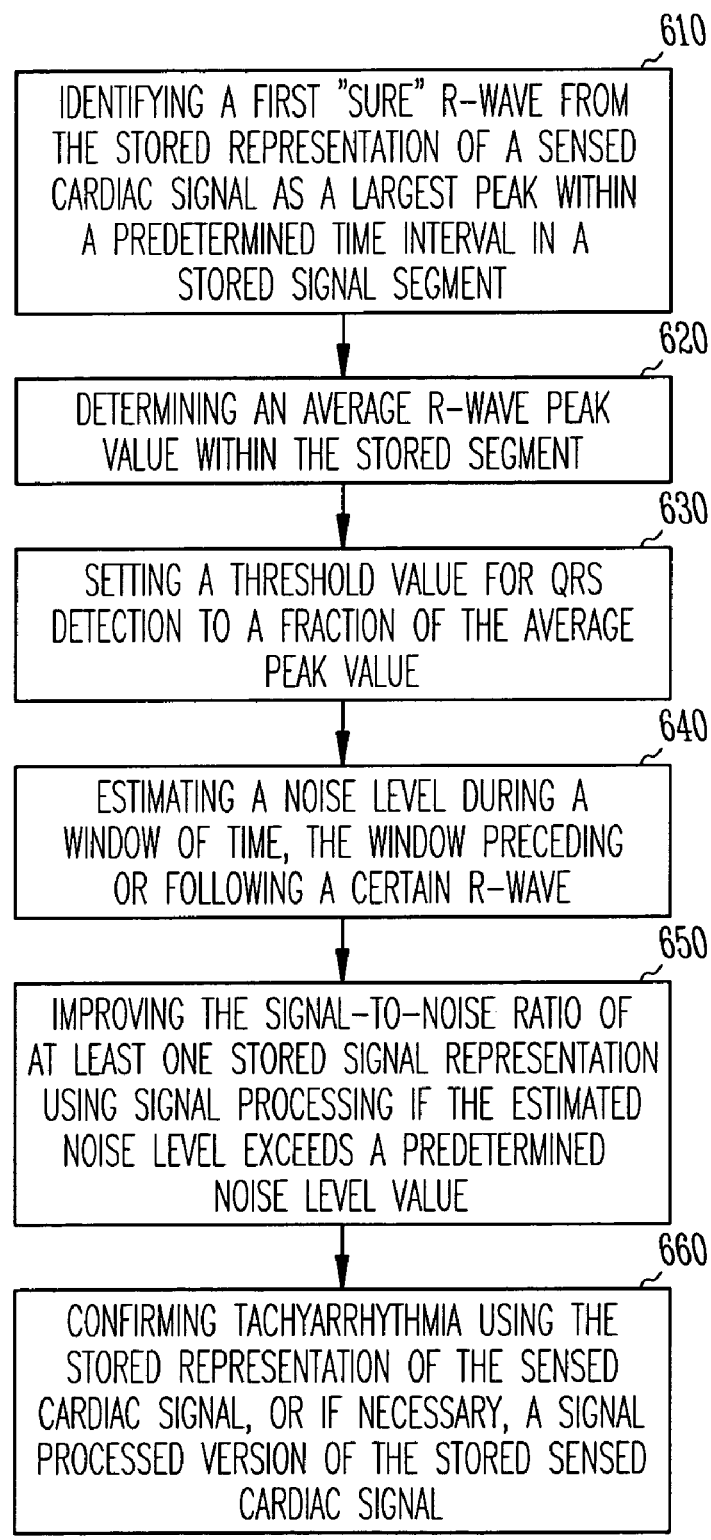
FIG. 6 shows a block diagram of an embodiment of a method for detecting tachyarrhythmia using stored representations of cardiac signals.

FIG. 6 shows a block diagram of an embodiment of a method 600 of using stored representations of cardiac signals to detect tachyarrhythmia. In some examples, the cardiac signals are EGMs sensed using a secondary sensing circuit. Analyzing stored EGMs is useful when the primary sensing circuit produces noisy signals. The stored signals from the secondary circuit may be less noisy, or the stored signals may be used to perform additional signal processing to confirm the tachyarrhythmia. At 610, a "sure" R-wave is identified from the stored representation of a sensed cardiac signal as a largest peak within a predetermined time interval in a stored signal segment. A "sure R-wave" refers to a high level of confidence that a signal artifact of a measured cardiac signal is an R-wave. In one example, a sure R-wave is identified as the peak amplitude value in every two-second segment within a predetermined time period segment. FIGS. 7A, 7B show graphs 700 of EGMs of cardiac signals. Graph 710 in FIG. 7A shows examples of the sure R-waves in an EGM of a cardiac signal 720 sensed from a sense vector to measure heart rate.

Returning to the method of FIG. 6, at 620, an average R-wave peak value is determined within the stored segment of the sampled signal by averaging the identified sure R-wave peak amplitudes. In some embodiments, the stored segment represents an intrinsic cardiac signal sampled for approximately eight to ten seconds. At 630, a threshold value for detecting other R-waves is set to a fraction of the average peak value. In some embodiments, the fraction is 33% of the average peak value. If the secondary sensing circuit detects tachyarrhythmia using this threshold, then tachyarrhythmia is confirmed.

Sometimes, it will be difficult to detect sure R-waves with specificity in the stored signal from the secondary circuit because of noise in the signal. Therefore, the method 600 includes determining the amount of noise on the stored signal and performing additional signal processing on the stored signal if the noise level exceeds a threshold value. At 640 a noise level is estimated during a window of time. The window of time is chosen preceding or following a sure R-wave. FIG. 7B shows an example of a noise detection window 750 preceding a sure R-wave 760.

In some examples, estimating a noise level during a window of time includes determining a number of times that the stored representation of sensed cardiac signal crosses a baseline value, such as a value of zero for example. Returning to the method of FIG. 6, at 650, if the estimated noise level exceeds a predetermined threshold level, the signal-to-noise ratio of at least one stored signal representation is improved using signal processing. The noise level exceeds a threshold level if a number of baseline crossings exceeds a threshold value of baseline crossings and the peak value is greater than the threshold value.

Figure 8:
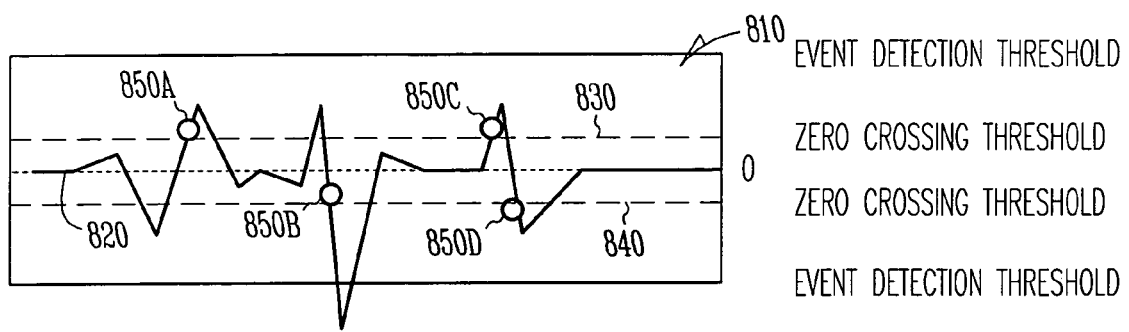
FIG. 8 is an illustration of a noise estimating technique.

FIG. 8 is an illustration 800 of a noise estimating technique using baseline crossings with zero as the baseline. A portion of the noise detection window 810 is shown containing a portion of the stored representation of the cardiac signal 820. A zero crossing threshold level is established in the positive direction 830 and the negative direction 840. When the cardiac signal traverses from the positive threshold 830 to the negative threshold 840, or vice versa, a zero crossing is deemed to have occurred. The crossings are indicated in the Figure by circles 850 A-D. Four zero crossings occur in the illustration 800. In one example, if the number of zero-crossings in a given time window exceeds a threshold value and the peak amplitude value is greater than the threshold value, then the noise level is deemed to be high. If the estimated noise level is deemed to be high, signal processing is used to improve the signal-to-noise ratio of the stored signal representation. In some examples, the signal processing includes low pass filtering. In some embodiments, signal processing is repeatedly applied to the same stored segment or segments. In some examples, the signal processing is performed by an IMD.

Returning to FIG. 6, at 660, tachyarrhythmia is detected using the stored representation of the sensed cardiac signal, or if the noise estimation determines that the signal is noisy, a signal processed version of the stored sensed cardiac signal with improved signal to noise ratio.

Figure 9:
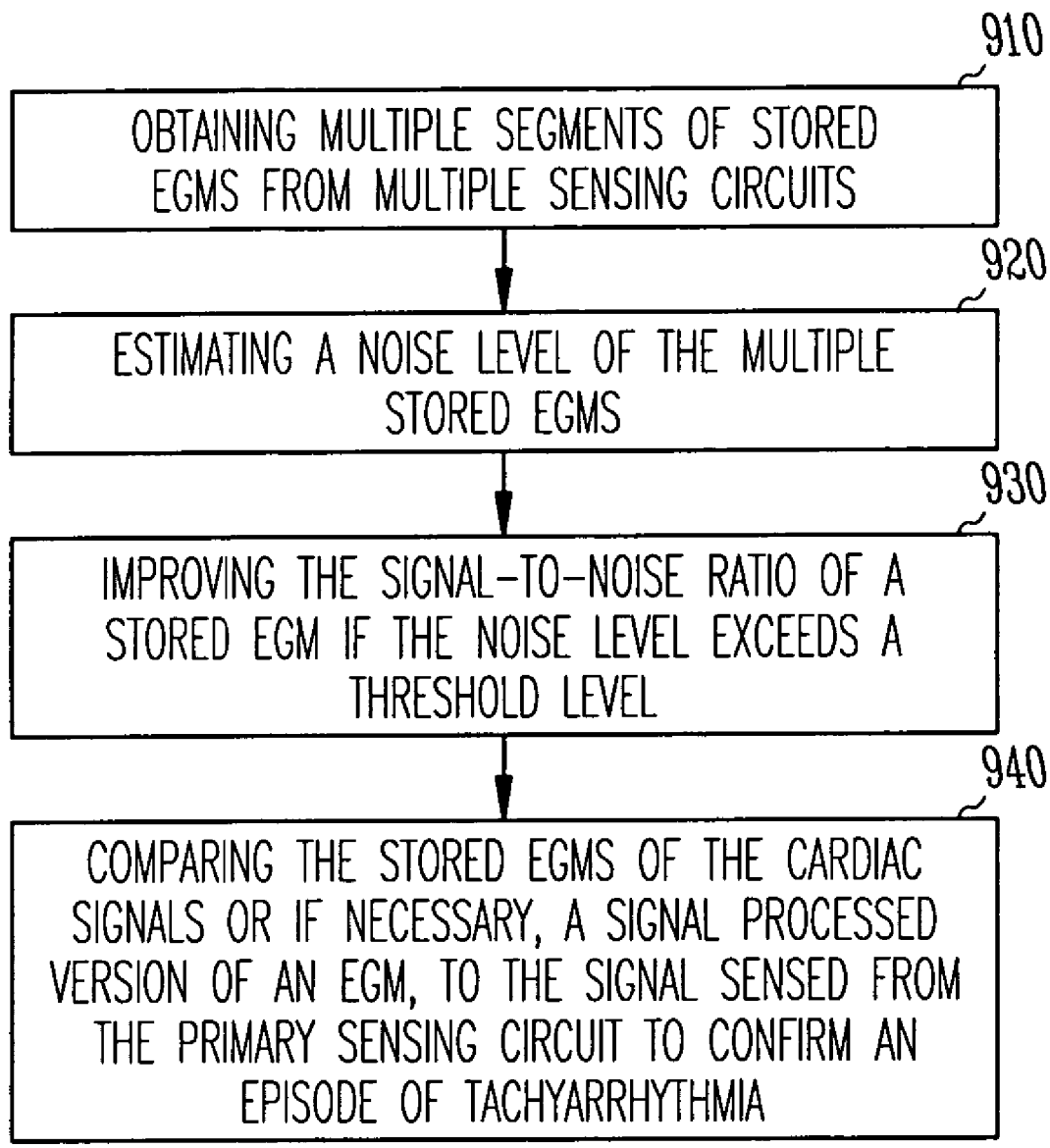
FIG. 9 shows a block diagram of an embodiment of a method for detecting tachyarrhythmia using multiple stored representations of cardiac signals.

In some method examples, stored EGMs obtained from additional sensing vectors are used to enhance tachyarrhythmia detection. FIG. 9 shows a block diagram of an embodiment of a method 900 for detecting tachyarrhythmia using stored representations of cardiac signals obtained from multiple sensing circuits. At 910, multiple segments of stored EGMs are obtained from multiple sensing circuits. Each EGM is obtained from a different sense vector. Each of the stored EGMs is compared to the signal sensed by a primary sensing circuit. At 920, a noise level of the multiple stored EGMs is estimated. At 930, if the noise level of a stored EGM exceeds a threshold level, the signal-to-noise ratio of the stored EGM is improved. At 940, the stored EGMs of the cardiac signals or if necessary, a signal processed version of an EGM, are compared to the signal sensed from the primary sensing circuit to confirm an episode of tachyarrhythmia. Tachyarrhythmia on the additional sense vectors can be determined using any of the methods discussed previously.

Figure 10:
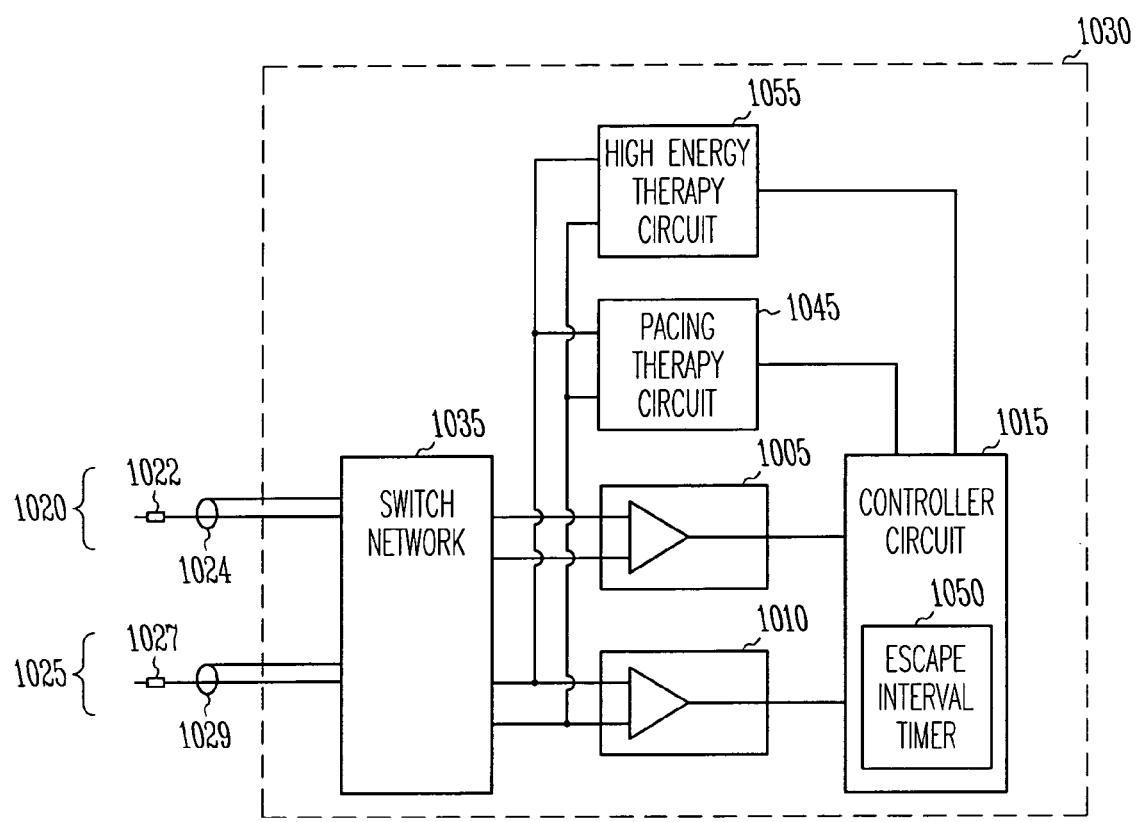
FIG. 10 shows a block diagram of an embodiment of a system to detect cardiac events.

The systems and methods are not limited to detection of tachyarrhythmia events, but may also provide simultaneous detection of tachycardia and bradycardia. Sensing circuits to detect tachyarrhythmia may be too sensitive to detect bradycardia rates, and sensing circuits for detecting bradycardia rates may not be sensitive enough to detect tachyarrhythmia. Because it is difficult to find a single sensitivity that is optimal for detecting both bradycardia (brady) and tachycardia (tachy), it is proposed to use two independent sensing sensitivities, the first for detecting bradycardia and the second for detecting tachycardia. This enhances bradyarrhythmia and tachyarrhythmia detection in ICDs that provide a combination of brady and tachy therapies, as well as brady devices (e.g., pacemakers) which also provide tachy episode detection and logging for diagnostic purposes. FIG. 10 shows a block diagram of an example of another system 1000 to detect cardiac events. The system 1000 comprises a first cardiac signal sensing circuit 1005 for sensing at least a first intrinsic cardiac signal, at least one second cardiac signal sensing circuit 1010 for sensing at least a second intrinsic cardiac signal, and a controller circuit 1015. The first and second sensing circuits monitor the same vector with the electrodes in communication with both the first and second sensing circuit. Switch network 1035 switches combinations of electrodes 1022, 1024, 1027, 1029 such as on cardiac leads 1020, 1025 or can electrode 1030 onto the sensing circuits 1005, 1010. The system 1000 further includes a pacing therapy circuit 1045 and a high energy therapy circuit 1055.

Preferably, the first sensing circuit 1005 senses intrinsic cardiac signal associated with depolarization of a first ventricle of a heart (i.e., it monitors a rate channel). The second sensing circuit 1010 has a higher sensitivity than the first sensing circuit 1005 and is used to detect tachyarrhythmia. In the preferred embodiment of detecting bradycardia events, the first and second sensing circuits sense cardiac signals from the same sense vector. In some embodiments, the first and second sensing circuits sense cardiac signals from different sense vectors.

Higher sensitivity refers to the second sensing circuit 1010 having a lower signal sensing threshold than the first circuit 1005, or the second sensing circuit 1010 providing greater amplification to detected cardiac signals, or the second sensing circuit 1010 having both a lower signal sensing threshold and providing greater amplification than the first sensing circuit 1005. Greater amplification also refers to the sensing circuits having automatic gain control (AGC) and the automatically determined gain of the second sensing circuit 1010 is greater than the gain of the first sensing circuit 1005.

Because the first and second sensing circuits monitor different sense vectors or the same vector at two different sensitivities, the controller circuit 1015 is able to make independent determinations of tachyarrhythmia and bradycardia using the second sensing circuit 1010 and the first sensing circuit 1005, respectively. In some examples, the system 1000 further includes a high-energy shock therapy circuit coupled to the controller circuit 1015, and the switch network 1035 is operable to connect a sensing vector that includes at least one electrode operable to deliver high-energy shock therapy to the second cardiac signal sensing circuit 1010.

The controller circuit 1015 makes one or more logical decisions about delivery of bradycardia pacing therapy and tachycardia therapy based on outputs of the first and second cardiac signal sensing circuits. The controller circuit 1015 includes an escape interval timer 1050. An escape interval timer 1050 is used in the treatment of bradycardia arrhythmias. The escape interval timer is reset whenever an intrinsic beat of the heart is detected. If the escape interval timer expires, it means the heart rate of the subject has dropped below a threshold rate or the heart of the subject has skipped a beat. When the timer 1050 expires, the controller circuit 1015 then initiates delivery of a paced beat from the pacing therapy circuit 1045.

Figure 11A:
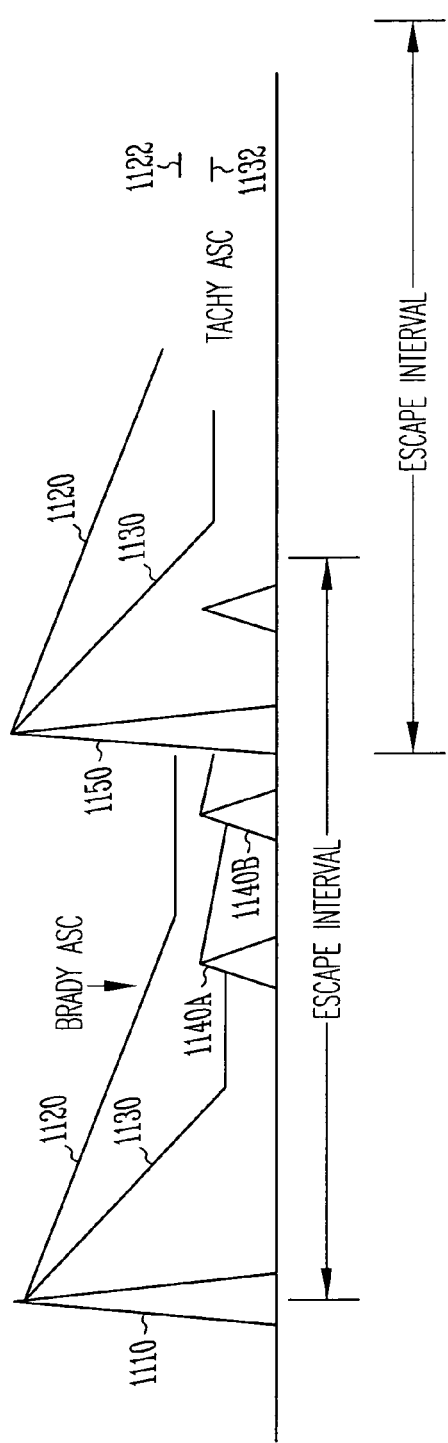
FIGS. 11A and 11B illustrate the operation of an escape interval timer.

In some examples, the controller circuit 1015 restarts the escape interval timer upon detecting a depolarization event if the depolarization event is sensed by both the first and second sensing circuits 1005, 1010. This is shown in the illustrations 1100 of FIG. 11A. Depolarization event 1110 is an R-wave that starts the escape interval timer 1050. Graph 1120 represents the declining signal sense threshold due to the automatic sensing control (ASC) of a depolarization sensing circuit, such as the first sensing circuit 1005. Graph 1130 represents the declining depolarization sensing threshold due to the ASC of a tachyarrhythmia (or tachy) sensing circuit, such as the second sensing circuit 1010. The graphs show that the tachy sensing circuit is more sensitive than the bradycardia arrhythmia (or brady) sensing circuit due to its having an ASC that decreases the sensing threshold more rapidly and to a lower final threshold level than the brady threshold level following detection of a depolarization. Level 1122 indicates the final sensing threshold level of the brady sensing circuit 1005 and 1132 indicates the final sensing threshold level of the tachy sensing circuit 1010. Because tachy sensing is more sensitive, the tachy sensing circuit detects events 1140 A, B that are not detected by the brady sensing circuit. Depolarization event 1150 is an R-wave sensed by both the tachy and brady sensing circuits and resets the escape interval timer 1050.

Figure 11B:
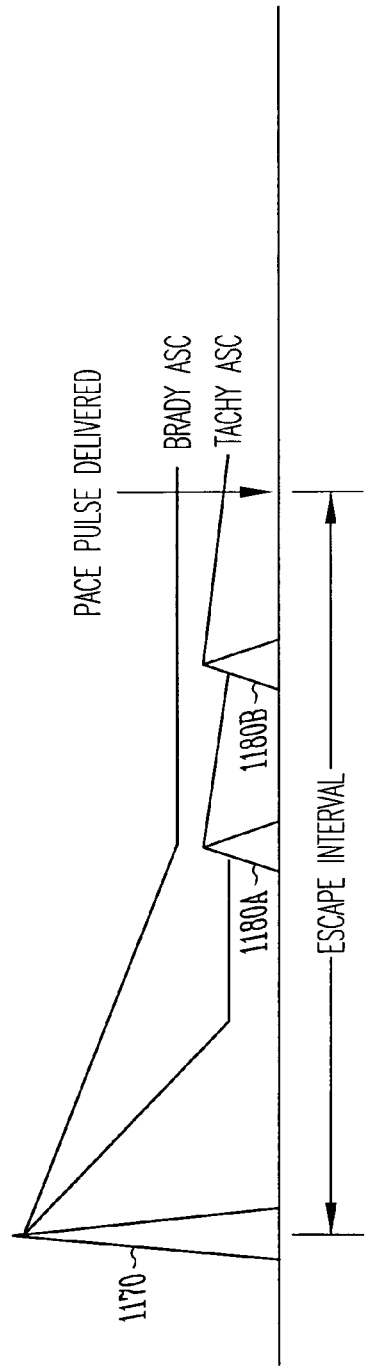

The controller circuit 1015 of FIG. 10 initiates pacing therapy upon expiration of the escape interval timer 1050 if a depolarization event is sensed only by the second sensing circuit 1010. This is useful if the second sensing circuit 1010 is detecting noise. This is shown by FIG. 11B. Depolarization event 1170 is an R-wave that starts the escape interval timer 1050. The second sensing circuit 1010 detects events 1180A and 1180B. However, because these events are not detected by the first sensing circuit, a pace pulse is delivered at the expiration of the escape interval.

Figure 12:
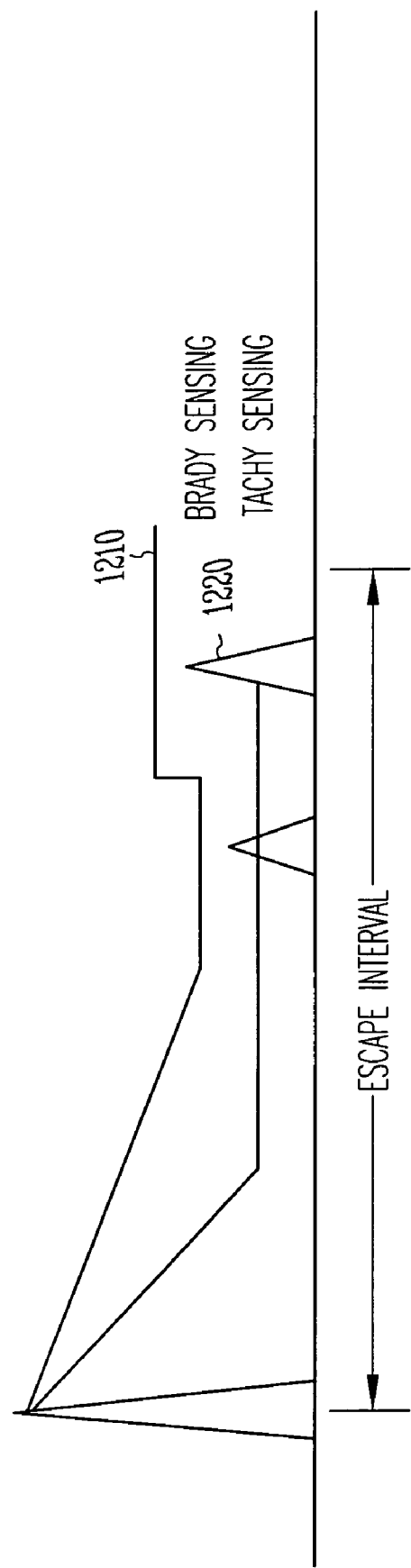
FIG. 12 illustrates adjusting the final sensing threshold of a sense amplifier.

If the second sensing circuit 1010 detects a depolarization event while the first sensing circuit 1005 does not detect the event, the second sensing circuit 1010 could be over-sensing depolarization events or the first sensing circuit could be under-sensing the event. Thus, in some examples, if a first depolarization event is sensed only by the second sensing circuit 1010, a subsequent depolarization event is sensed by both the first and second sensing circuits 1005, 1010, and the subsequent depolarization event is deemed a normal depolarization event, the controller circuit 1015 then deems these events sensed only by the second sensing circuit to be noise events. In one example of deeming a depolarization event a normal event, an R-R interval matches the expected R-R interval as determined from one or more immediately preceding intervals. In another example, the R-wave is deemed normal when the morphology of the R-wave, the peak value of the R-wave, or both the morphology and the peak value are normal. The events sensed by the more sensitive second sensing circuit are used for tachyarrhythmia detection. Because pacing pulse can be delivered between tachyarrhythmia events sensed by the second sensing circuit, the detection of tachyarrhythmia uses only the intervals between consecutive sensed events. The intervals between a sensed event and a paced event or a paced event and a sensed event are not used for tachyarrhythmia detection According to some system examples, sensing by a tachy sensing circuit 1010 can be used by the controller circuit 1015 to adjust a final sensing threshold on a brady sensing circuit 1005. An illustration 1200 of an example of the adjustment is shown in FIG. 12. If the tachy sensing circuit 1010 over-senses one or more events, the final sensing threshold 1210 of the brady circuit 1005 can be raised by the controller circuit 1015. This avoids sensing the detected peak 1220 as a depolarization using the brady sensing circuit 1005. As an example, the controller circuit 1015 could adjust the final threshold by writing a new value into a register. The new value could be increased by a multiple of the detected peak, such as to twice the detected peak for example, until the next paced event or the next intrinsic event is sensed by the first sensing circuit. The new final threshold level may be limited, for example, to twice the default final threshold level of the first sensing circuit. While this description has described separate tachyarrhythmia and bradycardia detection functions, these functions are combinable within one system such as a PG-ICD for example.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a primary cardiac signal sensing circuit operable to sense at least a first intrinsic cardiac signal, wherein the primary cardiac signal sensing circuit is configured to be coupled to a first and a second implantable electrode and has a first signal sensing sensitivity configured to detect bradycardia and a second higher sensitivity to simultaneously detect tachyarrhythmia;
   at least one secondary cardiac signal sensing circuit operable to sense at least a second intrinsic cardiac signal, wherein the secondary cardiac signal sensing circuit is configured to be coupled to at least a third implantable electrode different from the first and second electrode, has a higher signal sensing sensitivity than the primary sensing circuit, and is configured to detect ventricular tachycardia; and
   a controller circuit, coupled to the primary and secondary cardiac signal sensing circuits, the controller circuit operable to:
      detect tachyarrhythmia and bradycardia using the primary sensing circuit;
      detect tachyarrhythmia using the secondary sensing circuit; and
      deem the tachyarrhythmia valid if the controller circuit detects the tachyarrhythmia using both the primary and secondary sensing circuits.

2. The system of claim 1, wherein the controller circuit is operable to change the first sensitivity according to depolarization events sensed by the secondary sensing circuit.

3. The system of claim 1, wherein the controller circuit is operable to use the secondary sensing circuit to detect the tachyarrhythmia by shifting the second cardiac signal in time and multiplying the second cardiac signal and the first cardiac signal.

4. The system of claim 3, wherein the controller circuit is further operable to shift a cardiac signal in time to maximize an absolute peak of a multiplied signal.

5. The system of claim 1, wherein the secondary sensing circuit includes at least one electrode operable to deliver high energy shock therapy.

6. The system of claim 1, wherein the primary sensing circuit includes an electrode operable to sense intrinsic cardiac signals associated with a first ventricle and the secondary sensing circuit includes an electrode operable to sense intrinsic cardiac signals associated with a second ventricle.

7. The system of claim 1, wherein the primary sensing circuit includes a tip electrode and a ring electrode of a cardiac lead and the secondary sensing circuit includes a can electrode and one of a ring electrode or a tip electrode of another cardiac lead.

8. The system of claim 1, wherein the primary sensing circuit includes a tip electrode and a ring electrode of a cardiac lead and the secondary sensing circuit includes a can electrode and a shock therapy coil electrode.

9. The system of claim 1, wherein the secondary sensing circuit includes electrodes adaptable for placement across a myocardium of a patient, and wherein the controller circuit is operable to measure mechanical action of the heart using impedance signals sensed by the secondary sensing circuit.

10. The system of claim 1, wherein the secondary sensing circuit includes a wireless ECG system.

11. The system of claim 1, wherein the at least one secondary sensing circuit includes a plurality of secondary sensing circuits to detect tachyarrhythmia, and wherein the controller circuit is operable to deem the tachyarrhythmia valid using the primary sensing circuit and at least one of the plurality of secondary sensing circuits.

12. The system of claim 1, wherein the system further includes a therapy circuit coupled to the controller circuit, the controller circuit operable to initiate delivery of a therapy to the heart using the therapy circuit when the tachyarrhythmia is deemed valid.

13. The system of claim 1, wherein the system further includes a memory circuit to store representations of at least the first and second intrinsic cardiac signals, and wherein the controller circuit is operable to detect tachyarrhythmia using the primary sensing circuit and the secondary sensing circuit by analyzing the stored representations of the primary and secondary intrinsic cardiac signals.

14. The system of claim 13, wherein the controller circuit is operable to detect the tachyarrhythmia by shifting the stored second cardiac signal in time and multiplying the stored second cardiac signal and the stored first cardiac signal.

15. The system of claim 13, wherein the memory circuit includes a circular buffer, and the stored representations of intrinsic cardiac signals include representations of multiple cardiac cycles for a predetermined time duration.

16. The system of claim 13, wherein analyzing includes continuously analyzing the stored representations.

17. A method comprising:
   sensing a first intrinsic cardiac signal associated with a depolarization rate of a heart using a primary sensing circuit, the primary sensing circuit configured to be coupled to a first and a second implantable electrode and having a first signal sensing sensitivity configured to detect bradycardia and a second higher sensitivity configured to simultaneously detect tachyarrhythmia;
   sensing a second intrinsic cardiac signal of the heart using at least one secondary sensing circuit, wherein the secondary sensing circuit is configured to be coupled to a third implantable electrode different from the first and second electrode, has a higher signal sensing sensitivity than the primary sensing circuit, and is configured to detect ventricular tachycardia;
   detecting tachyarrhythmia using the primary sensing circuit;
   determining whether tachyarrhythmia is indicated by the secondary sensing circuit; and
   deeming the tachyarrhythmia as valid if both the primary and secondary sensing circuits indicate tachyarrhythmia.

18. The method of claim 17, including changing the first sensitivity according to depolarization events sensed by the secondary sensing circuit.

19. The method of claim 17, further including storing representations of the sensed signals, and wherein detecting tachyarrhythmia using the primary sensing circuit and determining using the secondary sensing circuit includes using stored representations of the signals.

20. The method of claim 19, wherein determining whether tachyarrhythmia is indicated by the secondary sensing vector includes:
- identifying a sure R-wave from the stored representation of the sensed cardiac signal as a largest peak within a predetermined time interval in a stored signal segment;
- determining an average sure R-wave peak value within the stored segment;
- setting a threshold value for R-wave detection to a fraction of the average sure peak value;
- estimating a noise level during a window of time, the window preceding or following a sure R-wave;
- improving the signal-to-noise ratio of the stored signal representation using signal processing if an estimated noise level exceeds a threshold noise level; and
- detecting tachyarrhythmia using the stored representation of the sensed cardiac signal, or if necessary, a signal processed version of the stored sensed cardiac signal.

21. The method of claim 20, wherein estimating a noise level during a window of time includes determining a noise amplitude and a number of times that a stored representation of a sensed signal crosses a baseline value, and wherein improving the signal-to-noise ratio of at least one stored signal representation includes improving the signal-to-noise ratio if a number of baseline crossings exceeds a threshold value of baseline crossings and the noise amplitude exceeds a threshold amplitude value.

22. The method of claim 17, wherein sensing the first and second intrinsic cardiac signals includes sensing using an implantable medical device.

23. The method of claim 22, wherein sensing the first and second intrinsic cardiac signals using an implantable medical device includes sensing using an implantable medical device that provides both cardioversion/defibrillation therapy and pacing therapy.

* * * * *

UNITED STATES PATENT AND TRADEMARK OFFICE
CERTIFICATE OF CORRECTION

PATENT NO. : 7,650,182 B2  
APPLICATION NO. : 11/177230  
DATED : January 19, 2010  
INVENTOR(S) : Kim et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 992 days.

Signed and Sealed this

Twenty-eighth Day of December, 2010

David J. Kappos
*Director of the United States Patent and Trademark Office*